(12) United States Patent
Sui et al.

(10) Patent No.: US 11,318,226 B2
(45) Date of Patent: May 3, 2022

(54) MATERIALS FOR PREPARING INTRAOCULAR LENS

(71) Applicant: EYEBRIGHT MEDICAL TECHNOLOGY (BEIJING) CO., LTD., Beijing (CN)

(72) Inventors: Xince Sui, Beijing (CN); Yongji Wei, Beijing (CN); Jiangbing Xie, Beijing (CN)

(73) Assignee: EYEBRIGHT MEDICAL TECHNOLOGY (BEIJING) CO., LTD., Beijing (CN)

( * ) Notice: Subject to any disclaimer, the term of this patent is extended or adjusted under 35 U.S.C. 154(b) by 0 days.

(21) Appl. No.: 15/776,263

(22) PCT Filed: Nov. 15, 2016

(86) PCT No.: PCT/CN2016/105819
§ 371 (c)(1),
(2) Date: May 15, 2018

(87) PCT Pub. No.: WO2017/084551
PCT Pub. Date: May 26, 2017

(65) Prior Publication Data
US 2019/0314547 A1    Oct. 17, 2019

(30) Foreign Application Priority Data

Nov. 19, 2015  (CN) .......................... 201510799170.5

(51) Int. Cl.
*A61L 27/18*    (2006.01)
*A61F 2/14*    (2006.01)
(Continued)

(52) U.S. Cl.
CPC .............. *A61L 27/18* (2013.01); *A61F 2/142* (2013.01); *A61F 2/145* (2013.01); *A61F 2/16* (2013.01);
(Continued)

(58) Field of Classification Search
CPC ......................................................... A61F 2/16
See application file for complete search history.

(56) References Cited

U.S. PATENT DOCUMENTS 5,008,102 A * 4/1991 York ..................... A61F 2/1613
351/159.63
6,326,448 B1  12/2001 Ojio
(Continued)

FOREIGN PATENT DOCUMENTS

CN        101484091       7/2009
CN        102065795       5/2011
(Continued)

OTHER PUBLICATIONS

Office Action corresponding to Chinese Application No. 201510799170.5 dated Mar. 5, 2019.
(Continued)

*Primary Examiner* — Michael F Pepitone
(74) *Attorney, Agent, or Firm* — Myers Bigel, P.A.

(57) ABSTRACT

The present invention relates to a material for preparing an intraocular lens. In particular, it relates to an ophthalmic medical material suitable for manufacture of micro-incision intraocular lens, having suitable water content and a suitable refractive index.

14 Claims, 3 Drawing Sheets

(51) Int. Cl.
 A61F 2/16 (2006.01)
 A61F 9/00 (2006.01)
 A61F 9/007 (2006.01)
 A61F 9/02 (2006.01)
 A61L 27/16 (2006.01)
 B29D 11/00 (2006.01)
 B29K 105/00 (2006.01)
 G02B 1/04 (2006.01)

(52) U.S. Cl.
 CPC ........ *A61F 9/0017* (2013.01); *A61F 9/00781* (2013.01); *A61F 9/02* (2013.01); *A61L 27/16* (2013.01); *B29D 11/00009* (2013.01); *A61F 2240/001* (2013.01); *A61L 2400/18* (2013.01); *B29K 2105/0002* (2013.01); *B29K 2995/0035* (2013.01); *G02B 1/043* (2013.01)

(56) References Cited

U.S. PATENT DOCUMENTS

| | | | |
|---|---|---|---|
| 6,329,485 | B1 | 12/2001 | Vanderbilt |
| 7,789,509 | B2 | 9/2010 | Mentak et al. |
| 8,247,511 | B2 | 8/2012 | Mentak |
| 2002/0049290 | A1* | 4/2002 | Vanderbilt .............. A61L 27/16 526/264 |
| 2013/0231740 | A1* | 9/2013 | Mentak .................... A61F 2/16 623/6.12 |
| 2013/0268072 | A1 | 10/2013 | Smith et al. |

FOREIGN PATENT DOCUMENTS

| | | |
|---|---|---|
| CN | 102460221 | 5/2012 |
| CN | 104024891 | 9/2014 |
| CN | 104725563 | 6/2015 |
| JP | 2011520561 | 7/2011 |
| JP | 2015515294 A | 5/2015 |
| WO | 00/34804 | 6/2000 |
| WO | 2004/000901 | 12/2003 |
| WO | 2009/143054 | 11/2009 |

OTHER PUBLICATIONS

Dehoog, Edward et al. "Evaluation of the Impact of Light Scatter from Glistenings in Pseudophakic Eyes," J Cataract Refract Surg, (2014) 40: 95-103.
Li, Zhao-Chun et al. "Intraocular lens opacification after cataract surgery," Int Rev Ophthalmol, 37(2):112-116 (Apr. 2013).
Office Action corresponding to Chinese Application No. 201510799170.5 dated Sep. 4, 2019.
Extended European Search Report corresponding to European Application No. 16865728.6 dated Jul. 4, 2019.
Office Action corresponding to Chinese Application No. 201510799170.5 dated Dec. 13, 2019.
Office Action corresponding to Japanese Application No. 2018-526180 dated Nov. 26, 2019.
Decision of Refusal issued in corresponding Chinese Patent Application No. 2018-526180, dated Jan. 26, 2021 (including English translation).
Office Action corresponding to Japanese Application No. 2018-526180 dated Aug. 4, 2020.

* cited by examiner

MATERIALS FOR PREPARING INTRAOCULAR LENS

STATEMENT OF PRIORITY

This application is a 35 U.S.C. § 371 national stage application of International Application Serial No. PCT/CN2016/105819, filed Nov. 15, 2016, which claims the benefit, under 35 U.S.C. § 119 (a) of Chinese Patent Application No. 201510799170.5, filed Nov. 19, 2015, the entire contents of each of which are incorporated by reference herein.

FIELD OF THE INVENTION

The invention relates to an ophthalmic medical material. In particular, it relates to an ophthalmic medical material suitable for manufacture of a micro-incision artificial lens, which has suitable water content and a suitable refractive index.

BACKGROUND OF THE INVENTION

Cataract patients can be surgically removed from the natural disease lens and implanted with an intraocular lens (also known as artificial lens), which can restore some or all of the vision. With the development of natural lens ablation techniques, incisions for surgery are getting smaller and smaller, generally 2-3 mm, and even less than 1.8 mm in recent years, so the incisions required for intraocular lens implantation should also be adapted. Small surgical incisions can heal in a short time, reduce patient's pain, and reduce postoperative astigmatism and other undesirable phenomena. Therefore, as cataract surgery increasingly develops toward the direction of micro incision, the requirements for the intraocular lens materials suitable for the micro incisions implantation are also increasing.

The intraocular lens materials have evolved over the decades, from the PMMA materials for the earliest production of hard intraocular lens to the silica gel, hydrogels (hydrophilic acrylates) and hydrophobic acrylates for the subsequent production of collapsible intraocular lens, they are better biocompatible materials (also known as polymer). However, due to the differences in the chemical and physical structures of each material, and the resulting differences in optical, mechanical and biological properties, there is a difference in the clinical performance of intraocular lens made of each material.

Silica gel is the earliest soft intraocular lens material used, which was widely used in the early 1990s. It has a stable structure, good tissue compatibility, excellent flexibility and elasticity, and can be folded to adapt to small incision implantation. However, silica gel intraocular lens have also shown many shortcomings in clinical use, for example, the refractive index of silica gel materials is low, and the refractive index of the improved silica gel materials can only be as high as 1.46. Therefore, the silica gel intraocular lens with the same diopter should be thicker; secondly, due to the high elasticity of the silica gel material, the folded silica gel intraocular lens may injure the patient's intraocular tissue due to excessive stretching after being implanted in the eye; in addition, the silica gel material is prone to adsorb silicone oil (an important ophthalmic surgery filler) and other substances.

The hydrogel material, also known as the hydrophilic acrylate material, is another kind of earlier used soft intraocular lens material, which has a smooth surface, good biocompatibility, a slight host anti-allogeneic cell response, and less deposition of macrophages and epithelioid cells. However, since the hydrogel intraocular lens material itself contains a large amount of water, the overall refractive index is also relatively low, so the intraocular lens is also relatively thick and cannot meet the requirements of smaller incisions. In addition, the water content of the existing hydrogel materials is generally high (18 to 34%), which leads to problems such as protein deposition and calcification inside the material (Li Zhaochun, Yao Ke, Xu Wen. Intraocular lens opacification after cataract surgery. International Ophthalmology Overview. 2013, 37(2): 112-116.) With the extension of usage time, the material will gradually become opaque and the probability of secondary cataracts will increase. At the same time, the hydrogel material contains too much water, which also greatly reduces the mechanical strength of the material itself, and its fracture strength is generally less than 2.5 MPa, this will lead to serious consequences for hydrogel intraocular lenses such as plication and rupture in the course of the folding implantation in the surgical use, especially pose challenges for the micro incision plantation (narrower implantation channel, greater push resistance).

Hydrophobic acrylate material is the most popular intraocular lens material on the market at present, and it has many advantages that silica gel material and hydrogel material do not have. Hydrophobic acrylates are a type of copolymer polymerized from acrylate monomers, methacrylate monomers, and other cross-linking monomers, which can have a refractive index up to 1.55. Therefore, for the intraocular lens with same diopter, it can be made thinner and more suitable for small incision implantation. The hydrophobic acrylates lens is moderately elastic and takes about 3-5 seconds from the folded state to fully unfolded, so it is safer to operate. In view of the comprehensive advantages of hydrophobic acrylates, it has become the most popular intraocular lens material on the market. Nonetheless, hydrophobic acrylates also have deficiencies as an intraocular lens material. First of all, although hydrophobic acrylate materials can achieve higher refractive index, as the refractive index of the material increases, the dispersion effect of the materials will also increase, and the glare effect after processing into intraocular lens will be correspondingly heavier, so the refractive index of the material cannot be increased without limit; secondly, the intraocular lens made of partially hydrophobic acrylate material has a serious glistenings phenomenon (Edward DeHoog, Anand Doraiswamy. Evaluation of the Impact of Light Scatter from Glistenings in Pseudophakic Eyes. J Cataract Refract Surg. 2014, 40: 95-103); most importantly, hydrophobic acrylate materials have higher surface tackiness and are harder materials, therefore, compared with silica gel and hydrogels, they have neither the flexibility nor the extensibility of silica gel materials, and they are not as smooth as the hydrogel material, which results in the intraocular lens made of the hydrophobic acrylate material causing great stress and friction when passing through the narrow channel of the implant head, which is not favorable for the micro-incision implantation. Combining these above factors means that as cataract surgical incisions become smaller and smaller, hydrophobic acrylics are increasingly limited. Therefore, there is a great need for a new type of intraocular lens materials that combine the advantages of the above materials to overcome its shortcomings.

U.S. Pat. Nos. 7,789,509 and 8,447,511 each disclose an anti "glistening" intraocular lens material and an aqueous plasticized intraocular lens material, both of which are based on the improvements made on hydrophobic acrylate materials. "glistening" is a reflection of the defects present in certain hydrophobic acrylate materials. When the intraocular lens made of these materials is implanted into the human eye, after soaking in the aqueous humor environment for some time, there will be some punctate vesicles of different sizes inside of the materials, especially when they are observed under slit lamp or other equipment, they exhibit "glistening" characteristics, and are therefore called "glistening." After a cataract patient is implanted with a intraocular lens having "glistening", vision will be seriously affected or even blinded after a period of time. U.S. Pat. No. 7,789,509 added a small amount of hydrophilic monomer to the hydrophobic acrylate material, so that the material itself can have a lower water content (about 4%), so as to avoid the "glistening" of the intraocular lens after soaking in the aqueous humor, and also maintains the basic properties of hydrophobic acrylate materials. U.S. Pat. No. 8,247,511 believes that the existing hydrophobic acrylate materials have many drawbacks, mainly because the hydrophobic acrylate materials need to have a lower glass transition temperature in order to meet the foldability during the surgery, but this will increase the difficulty of processing the material into intraocular lenses, because the material needs to maintain a firm state during the turning or polishing process, and the ordinary room temperature environment cannot provide a firm state of the material, so it is necessary to process the material under additional low temperature conditions. In response to these problems, U.S. Pat. No. 8,247,511 also incorporated a small amount of hydrophilic monomer in the hydrophobic acrylate material, so that the material itself can have less water content (about 4%), so that the material has a higher glass transition temperature in dry conditions, and it is in a hard state at room temperature, enables turning and polishing to be performed on the intraocular lens while it has good flexibility under hydration (wet) conditions and can be folded during the implantation procedure. From the above cases, it can be found that the hydrophobic acrylate is still highly recognized as an intraocular lens material, but due to its many drawbacks, it needs to be improved to adapt to the development of cataract surgery. In the above cases, a small amount of hydrophilic monomer was added into the hydrophobic acrylate materials, so that the materials have a water content, but the water content of these materials is very low (about 4%); it is just a small improvement for the hydrophobic acrylate materials, and the materials still have greater limitations after processing into intraocular lens. Because of the low water content in the materials, the materials still exhibit hydrophobic acrylate properties, such as higher surface tackiness, harder materials, etc., so the intraocular lens with too low water content will still produce great stress and friction when it passes through the very narrow channel of the implantation head.

SUMMARY OF THE INVENTION

At this stage, the only effective method for the treatment of cataract is the implantation of an intraocular lens to replace the cloudy natural lens of the human eye. Modern cataract surgery is generally divided into two steps: the first step is to remove the natural lens of the human eye by phacoemulsification, and the second step is to implant the intraocular lens in the capsular bag of the human eye. With the development of cataract surgery, the incision required for phacoemulsification has been developing to a trend of micro incision below 2.0 mm. However, the intraocular lens products on the current market are still unable to perfectly satisfy the micro incision surgery. The present invention provides a material, intraocular lens really suitable for micro-incision cataract surgery (i.e. a flexible intraocular lens or a flexible IOL).

The present invention provides a medical material (such as a material for preparing an intraocular lens) that is truly applicable to a micro-incision cataract surgery, overcoming the defects of the mainly used hydrophobic acrylates materials and hydrophilic acrylates materials (hydrogel) in the current market. The present invention adds a moderate content of hydrophilic monomer into the hydrophobic acrylates material, so that the material has a suitable water content (5 to 15 wt %). Because of the moderate water content, the medical material provided by the present invention (for example, the materials for the preparation of intraocular lens) combines the mechanical strength of the hydrophobic material with the lubricity and flexibility of the hydrophilic material, and is suitable for an intraocular lens for micro incision cataract surgery. In addition, through the selection and proportioning of monomers, the material has a suitable refractive index (1.49 to 1.54) so that the intraocular lens made of the material can maintain a relatively thin thickness. In addition, the material has a suitable glass transition temperature, so that the material has low requirements of the processing temperature and other conditions. In addition, the material has no glistening phenomenon, no calcification, no protein deposition and other phenomena, and it is particularly suitable for the manufacture of micro-incision intraocular lens.

The present invention relates to a material, in particular, an ophthalmic medical material suitable for the manufacture of a micro-incision intraocular lens having a suitable water content and a suitable refractive index, which is prepared by copolymerizing acrylates monomers, wherein the acrylates monomers contain hydrophilicity acrylates monomers and hydrophobic acrylates monomers, wherein the molar ratio of the hydrophilic monomers and the hydrophobic monomers is from 20:80 to 80:20, preferably from 30:70 to 70:30, more preferably from 40:60 to 60:40, the materials have the following specific properties:

a. the water content at 35° C. is 5-15 wt %, preferably 6-13 wt %, more preferably 7-12 wt %, even 8-11 wt %, especially 9-11 wt %;

b. the refractive index (wet state) at 35° C. is 1.49-1.54, preferably 1.49-1.53, more preferably 1.50-1.52.

DETAILED DESCRIPTION

The hydrophilic acrylates monomer of the material of the present invention (for example, a material for preparing an intraocular lens) is selected from the group consisting of acrylates monomers having hydrophilic group(s), which conforms to the following formula:

wherein $R_1$ is H or $C_{1-6}$ alkyl, preferably H or $CH_3$;

$R_2$ is a linear or branched, saturated or unsaturated $C_{1-20}$ alkyl or $C_{6-20}$ arylalkyl, or a linear or $C_{6-20}$ heteroarylalkyl;

X may be O, S or $NR_4$, wherein $R_4$ is H, linear or branched, saturated or unsaturated $C_{1-20}$ alkyl or $C_{6-20}$ arylalkyl, or $C_{6-20}$ heteroarylalkyl, or $C_{3-20}$ heterocyclylalkyl;

$R_3$ is $C_nH_{2n+1}O_m$, wherein m or n is equal to 0 or is selected from an integer greater than 1, and m≤n, or $C_{3-20}$ heterocyclylalkyl or $C_{3-20}$ cycloalkyl.

The material of the present invention (for example, a material for preparing an intraocular lens), wherein the hydrophilic acrylate is an acrylate having a hydrophilic group and is selected from, for example, hydroxyethyl methacrylate, hydroxyethyl acrylate, hydroxypropyl methacrylate, hydroxypropyl acrylate, vinyl pyrrolidone, ethoxyethoxyethyl methacrylate, ethoxyethoxyethyl acrylate, ethoxyethyl methacrylate, ethoxyethyl acrylate, methoxyethyl methacrylate, methoxyethyl acrylate, 1,3-butylene glycol dimethacrylate, ethylene glycol dimethacrylate, polyethylene glycol methacrylate, polyethylene glycol 200 dimethacrylate (eg AGEFLEX' PEG200DMA), polyethylene glycol acrylate, poly(ethylene lone glycol) methyl ether methacrylate, polyethylene glycol methyl ether acrylate, glycidyl methacrylate, glycidyl acrylate, acrylic acid, methacrylic acid, 2-(trifluoromethyl) acrylic acid, phenyl acrylic acid, acrylamide, methacrylamide, N-methylol acrylamide, N-methylol methacrylamide, or derivatives thereof, or a mixture thereof. Hydroxyethyl methacrylate is preferred.

The hydrophobic acrylates monomer of the material of the present invention (for example, the material for preparing an intraocular lens) is selected from the group consisting of acrylates monomers having hydrophobic group(s), which conforms to the following formula:

wherein $R_1$ is H or $C_{1-6}$ alkyl, preferably H or $CH_3$;

$R_5$ is linear or branched, saturated or unsaturated $C_{1-20}$ alkyl or $C_{6-20}$ arylalkyl, or $C_{6-20}$ heteroarylalkyl, or $C_{6-20}$ heterocyclylalkyl or $C_{3-20}$ cycloalkyl;

Y may be H, or Z—$R_6$, where Z may be present or absent and may be selected from heteroatoms such as O or S;

$R_6$ is $C_{6-20}$ arylalkyl, or $C_{6-20}$ heteroarylalkyl.

The material of the present invention (for example, a material for preparing an intraocular lens), wherein the hydrophobic acrylates are an acrylate having hydrophobic group(s) and is selected from, for example, methyl methacrylate, ethyl methacrylate, ethyl acrylate, butyl methacrylate, butyl acrylate, hexyl methacrylate, hexyl acrylate, isopropyl methacrylate, isopropyl acrylate, isobutyl methacrylate, isobutyl acrylate, tert-butyl methacrylate, tert-butyl acrylate, isooctyl methacrylate, isooctyl acrylate, isodecyl acrylate, isodecyl methacrylate, lauryl methacrylate, lauryl acrylate, octadecyl methacrylate, octadecyl acrylate, 9-anthryl methyl methacrylate, 9-anthryl methyl acrylate, cyclohexyl methacrylate, cyclohexyl acrylate, dimethylaminoethyl acrylate, dimethylaminoethyl methacrylate, N,N-dimethylmethacrylamide, N,N-dimethylacrylamide, N,N-diethylaminoethyl acrylate, N,N-diethylaminoethyl methacrylate, N-tert-butyl acrylamide, N-tert-butyl methacrylamide, N-isopropyl acrylamide, N-isopropyl methacrylamide, tetrahydrofurfuryl methacrylate, tetrahydrofurfuryl acrylate, trifluoroethyl methacrylate, trifluoroethyl acrylate, hexafluorobutyl methacrylate, hexafluorobutyl acrylate, 2-perfluorodecylethyl acrylate, 2-perfluorodecylethyl methacrylate, 2-(perfluorooctyl)ethyl methacrylate, 2-(perfluorooctyl)ethyl acrylate, acetone glycidyl methacrylate, acetone glycidyl acrylate, tetrahydrofuryl acrylate, tetrahydrofurfuryl methacrylate, phenyl methacrylate, phenyl acrylate, phenylethyl methacrylate, phenylethyl acrylate, phenoxyethyl methacrylate, phenoxyethyl acrylate, benzyl methacrylate, benzyl acrylate, acetoacetoxyethyl methacrylate, acetoacetoxyethyl acrylate, diacetone acrylamide, diacetone methacrylamide, allyl methacrylate, phenoxyethyl acrylate, or a derivative of the above substances, or a mixture of the above substances. Ethyl acrylate and/or phenoxyethyl acrylate are preferred.

The materials of the present invention (e.g. materials for preparing intraocular lens), if necessary, should also contain one or more additives such as cross-linking agents, UV absorbents, blue light absorbents, and the like.

The material of the present invention (for example, a material for preparing an intraocular lens) may contain a cross-linking agent, wherein the cross-linking agent is selected from polymerizable monomers having two or more functionalities, including: ethylene glycol dimethacrylate, ethylene glycol diacrylate, butanediol dimethacrylate, butanediol diacrylate, hexanediol dimethacrylate, hexanediol diacrylate, diethylene glycol dimethacrylate, diethylene glycol diacrylate, triethylene glycol dimethacrylate, triethylene glycol diacrylate, polyethylene glycol dimethacrylate, polyethylene glycol diacrylate, trimethylolpropane triacrylate, trimethylolpropane trimethacrylate, triethylolpropane triacrylate, triethylolpropane trimethacrylate, bisphenol A glycerol dimethacrylate, bisphenol A glycerol diacrylate, pentylene glycol diacrylate, pentanediol dimethacrylate, methacrylic anhydride, acrylic anhydride, N,N'-methylenebisacrylamide, N,N'-methylenedimethyl acrylamide, divinyl benzene, or derivatives of the above substances or mixtures thereof. Diethylene glycol dimethacrylate is preferred.

The material of the present invention (for example, a material for preparing an intraocular lens) may contain an ultraviolet absorbent, wherein the ultraviolet absorbent is selected from compounds having an efficient absorption function for ultraviolet rays having a wavelength in the range of 380 nm or less. Preferred are highly safe benzophenone compounds and/or benzotriazole compounds. More preferred are benzophenone-based compounds and/or benzotriazole-based compound compounds having polymerizable groups selected from the group consisting of vinyl, allyl, butenyl, ethynyl, acryloyloxy, methacryloxy, acrylamide, methacrylamide, vinyl ether group, and the like.

The material of the present invention (for example, a material for preparing an intraocular lens) may contain a blue light absorbent, wherein the blue light absorbent is selected from compounds having a selective filtration function for blue light in a wavelength range of 400 to 500 nm. The yellow dye-based compound containing an azo group in the molecular structural formula is preferable. More preferred is a yellow dye compound containing a polymerizable group selected from the group consisting of vinyl, allyl, butenyl, ethynyl, acryloyloxy, methacryloxy, acrylamide, methyl acrylamide, vinyl ether group, etc.

The material of the present invention (for example, a material for preparing an intraocular lens) is obtained by polymerization of a hydrophobic acrylate monomer, a hydrophilic acrylate monomer, and optional additives such as a cross-linking agent, an ultraviolet absorbent, a blue light absorbent, and the like. Among them, the polymerization method is selected from the group consisting of bulk polymerization, preferably free radical bulk polymerization. Radical polymerization initiators may be chosen to be free radical polymerization initiators common in the art, selected for example from azo initiators, and/or peroxo initiators, preferably dilauroyl peroxide, bis(4-tert-butylcyclohexyl) peroxydicarbonates, di(hexadecyl)peroxydicarbonates, di(tetradecyl) peroxydicarbonates, azobisisobutyronitrile, azobisisovaleronitrile, azobisisoheptonitrile, dicumyl peroxide, benzoyl peroxide 2,5-dimethyl-2,5-di(t-butylperoxy) hexane, tert-butyl peroxy-carbonate 2-ethylhexyl esters, tert-amyl peroxy-2-ethyl hexanoate, tert-amyl peroxy(2-ethylhexyl)carbonate, 2,5-dimethyl-2,5-bis(2-ethylhexanoic acid peroxy) hexane, 2,5-dimethyl-2,5-di-tert-butyl peroxy-3-hexyne, tert-butyl peroxy (2-ethyl hexanoate), 1,1-di-tert-butyl peroxycyclohexanone, tert-butyl peroxyneodecanoate, tert-butyl peroxypivalate, t-butyl 2-ethylbutane peroxycarboxylate, 1,1-di-tert-butylperoxy-3,3,5-trimethylcyclohexane, 3,6,9-tri ethyl-3,6,9-trimethyl-1,4,7-triperoxynonane, bis (3,5,5-trimethylhexanoyl)peroxide, 1,1,3,3-tetramethylbutyl peroxy 2-ethylhexanoate, tert-butyl peroxy-3,5,5-trimethyl hexanoate, tert-butyl hydroperoxide, di-tert-butyl peroxide, tert-butyl peroxybenzoate, tert-butylperoxyisopropyl formate, di(2-ethylhexyl)peroxydicarbonate, tert-butyl peroxyacetate, hydroxy cumene peroxide, diisopropylbenzene hydroperoxide, tert-butyl isopropyl peroxide, pentyl hydroperoxide or mixtures thereof. Azobisisobutyronitrile is preferred.

The material of the present invention (for example, a material for preparing an intraocular lens) has a moderate water content, provides the necessary lubricity and flexibility for the intraocular lens to be suitable for the micro incision operation, and does not cause severe negative effect on the refractive index and the mechanical properties of the intraocular lens at the same time. Therefore, the material of the present invention (for example, a material for preparing an intraocular lens) has a saturation water content selected from 5 to 15% by weight, preferably 6 to 13% by weight, and more preferably 7 to 12% by weight, even 8-11% by weight, especially 9-11% by weight, in simulated human intraocular state (35° C. physiological saline).

The material of the invention (for example, the material for preparing an intraocular lens) has a moderate refractive index and can be processed into a thinner intraocular lens with equivalent diopter, so that it is more suitable for a micro incision implantation operation; at the same time, it overcomes the dispersion effect caused by too high refractive index, and then prevents glare after intraocular lens implantation. Therefore, the material of the present invention (for example, a material for preparing an intraocular lens) has a refractive index selected from the range of 1.49 to 1.54, preferably 1.49 to 1.53, and more preferably 1.50 to 1.52 in a simulated human intraocular state (35° C. physiological saline).

The materials of the present invention (for example, materials for the preparation of intraocular lens) have special mechanical properties, appear as a hard material in a dry environment at room temperature or below, and can be processed into an intraocular lens; and in a wet state (after complete hydration) at room temperature or in simulated human eye (35° C.) environment, appear as a soft material that can be folded to enter the human eye's capsular bag through a narrow channel. It can then automatically and slowly return to the original shape of the intraocular lens and remain stable working status in the capsular bag. Therefore, the material of the present invention (for example, a material for preparing an intraocular lens) has a dry glass transition temperature selected from 10 to 35° C., preferably 15 to 30° C., more preferably 20 to 25° C.; the material of the present invention (e.g., the preparation of an intraocular lens) has moderate mechanical strength, and its elongation at break in the wet environment (completely hydrated) at room temperature is at least 180%, and the breaking strength is at least 2.5 MPa, which can meet the requirements of micro-incision surgical implantation, and avoids the occurrence of folding haptics and/or fracture of haptics, etc. during the implantation of the intraocular lens to ensure intraoperative safety.

The inventors of the present invention have found that the intraocular lens material finally obtained by the selection and proportioning of monomers can have the above-mentioned comprehensive properties, and have the following properties simultaneously:

a. the water content at 35° C. is 5-15 wt %, preferably 6-13 wt %, more preferably 7-12 wt %;

b. the refractive index (hydrate) at 35° C. is 1.49-1.54, preferably 1.49-1.53, more preferably 1.50-1.52. The material of the present invention (for example, a material for preparing an intraocular lens) has a molar ratio of a hydrophilic monomer to a hydrophobic monomer of 20:80 to 80:20, preferably 25:75 to 75:25, and preferably 30:70 to 70:30, preferably 35:65-65:35, preferably 40:60-60:40, more preferably 45:55-55:45, even about 50:50. Without wishing to be bound by any theory, the refractive index formula of the copolymer is:

$$n = \sum_i v_i n_i,$$

wherein $$\sum_i v_i = 1,$$

is the volume fraction of each component, $n_i$ is the refractive index of each component, and the refractive index of the hydrophilic acrylate material after water saturation can be approximately apply this formula: $n = v_w n_w + (1-v_w)n_p$, wherein $V_w$ is the volume fraction of water (approximate water content), $n_w$ is the refractive index of water, and $n_p$ is the refractive index of the dry acrylate polymer. On this basis, the proportions of the hydrophobic monomer and the hydrophilic monomer are adjusted so that the material of the present invention conforms to the water content and the refractive index.

The materials of the present invention (for example, materials for preparing intraocular lens) may further include at least one fluorescent agent and/or at least one photosensitizer.

When the material of the present invention contains a fluorescent agent, the fluorescent agent is fixed inside or on the surface of the final material. The fluorescent agent is stably combined in the final material, in which case the fluorescence of the material of the invention can be utilized; for example, a medical test can be performed. Specifically, the material is fluoresced under a slit lamp light source or a Pentero microscope, and the ophthalmologist can clearly and distinctly determine the adaptability of the material to the cornea. Since the material does not stain the cornea by contacting the cornea, the exfoliating corneal fluorescent dye is thoroughly eliminated, so that the medical test using the material of the present invention does not need to add any additional reagents (including fluorescent agents).

When the material of the present invention contains a photosensitizer, the photosensitizer is fixed inside or on the surface of the final material, and the material is implanted into the lesion by surgery. When the lesion is to be treated, the laser of the selected wavelength is irradiated to the lesion; when the treatment is finished, only the laser needs to be removed. Because the photosensitizer is trapped inside or on the surface of the material and cannot freely enter into other tissues of the human body via blood or other body fluids, the toxicity of the photosensitizer itself can be ignored, and the selection range of the photosensitizer is no longer limited. In particular, the material provided by the present invention may be implanted in advance into possible tissues or sites along with other eye surgeries: on the one hand, it can play a preventive role, on the other hand, once the tissue or site is onset, the laser treatment can be conducted immediately without performing the operation again; more specifically, the material provided by the present invention has a repetitive effect, and when a laser treatment is completed, since the photosensitizer is not eliminated and remains in the lesion site, when the posterior lesions occurs in the site once again or more than once, multiple laser treatments can be performed again or multiple times without the need for multiple injections of photosensitizers, with treatment repeatability.

In the material of the present invention (for example, a material for preparing an intraocular lens), when a copolymer obtained by copolymerizing acrylate monomers as a copolymer material, it further contains at least one fluorescent agent and/or at least one photosensitizer, the combination mode of the fluorescent agent and/or the photosensitizer with the copolymer material is selected from the group consisting of:

the fluorescent agents and/or photosensitizers participate in the polymerization during the forming of the copolymer material;

the fluorescent agents and/or photosensitizers are added to the copolymer material by physical dispersion during the forming of the copolymer material;

the fluorescent agents and/or photosensitizers are fixed on the surface of the copolymer material by surface grafting and surface modification; and/or the fluorescent agents and/or photosensitizers are fixed on the surface of the copolymer material by surface-coating mode.

When (1) the fluorescent agents and/or the photosensitizers are combined with the copolymer material in such a manner that the fluorescent agents and/or the photosensitizers participate in the polymerization during the forming of the copolymer material, the fluorescent agents and/or the photosensitizers comprise a polymerizable monomer material.

When (2) the fluorescent agents and/or photosensitizers are combined with the copolymer material in such a manner that the fluorescent agents and/or photosensitizers are added into the copolymer material by physical dispersion during the forming of the copolymer material, the fluorescent agents and/or the photosensitizers may be any suitable fluorescent agents and/or photosensitizers, optionally containing polymerizable monomers.

When (3) the fluorescent agents and/or the photosensitizers are combined with the copolymer material in such a manner that the fluorescent agents and/or the photosensitizers are surface-grafted and surface-modified on the surface of the formed copolymer material, the copolymer material is a shaped material, but the polymerizable groups are contained on the surface of the copolymer material.

The polymerizable groups herein may be, for example, vinyl, allyl, butylene, acryloxy, methacryloxy, acrylamido, methacrylamido, vinyl ether group, alkynyl, hydroxy, mercapto, amino, imino, carboxyl, anhydride, aldehyde group, isocyanate group, siloxane group, epoxy, cyclic nitrogenous group, and the like.

When (4) the fluorescent agents and/or the photosensitizers are combined with the copolymer material in such a manner that the fluorescent agents and/or photosensitizers are fixed on the surface of the shaped copolymer material by surface-coating, the copolymer material is a shaped material.

In one embodiment of the present invention, the fluorescent agent of the present invention is selected from the group consisting of fluorescein (sodium), cyanine fluorescent dyes, fluorescein isothiocyanate, rhodamine substances with fluorescent properties, lanthanide chelates with fluorescence characteristics, P-phycoerythrin (PE), substances that produce fluorescence upon enzyme action, such as Polypida chlorophyllin (PerCP), propidium iodide, and others derivatives that have an emission wavelength of 300-850 nm and are based on the modification of the above fluorescent agent, or a fluorescent agent formed by properly loading the above compound into a nanomaterial, or a mixture thereof.

In one embodiment of the present invention, the photosensitizer of the present invention is selected from photodynamic type photosensitizers or photothermal type photosensitizers. The photosensitizer of the present invention is any photosensitizer with an activation wavelength range of 300 to 1100 nanometers of the laser light source. Preferably, the wavelength range of the laser light source is selected from 500 to 1000 nanometers; preferably, the wavelength range of the laser light source is selected from 600 to 900 nanometers; preferably, the wavelength range of the laser light source is selected from 700 to 900 nanometers or the wavelength range of the laser light source is selected from 800 to 1100 nm.

In one embodiment of the present invention, when the material containing a photodynamic type photosensitizer according to the present invention is irradiated with laser light of a selected wavelength (e.g., 300 to 1100 nanometers), the photosensitizer in the material is excited to generate a cytotoxic active oxygen species, which can kill the cells on the lesion site, to achieve the therapeutic effect.

In another embodiment of the present invention, when the material containing the photothermal type photosensitizer according to the present invention is irradiated with laser light of a selected wavelength (for example, 300 to 1100 nanometers), the photosensitizer in the material is excited, and light energy is converted into heat, which increases the ambient temperature to kill the diseased tissue cells. When the temperature of the diseased tissue area reaches 43° C., DNA, RNA, and protein synthesis can be inhibited. The safety margin of normal cells is 45° C. Therefore, in a preferred embodiment, the material containing the photothermal type photosensitizer can generate heat under the irradiation of laser light to increase the temperature by 4 to 20° C.; in a more preferred embodiment, the material containing the photothermal type photosensitizer can generate heat under the irradiation of laser light to increase the ambient temperature by 6 to 12° C.; in a more preferred embodiment, the material containing the photothermal type photosensitizer can generate heat under the irradiation of the laser to increase the ambient temperature by 8 to 10° C. For example, the elevated temperature is more than 38° C., more than 39° C., preferably more than 40° C., preferably more than 41° C., preferably more than 42° C., preferably more than 43° C., preferably more than 44° C., preferably more than 45° C., preferably more than 46° C., preferably more than 47° C., preferably greater than 50° C., and less than 55° C., preferably greater than 56° C., preferably greater than 57° C., preferably greater than 58° C., preferably greater than 59° C., preferably greater than 60° C., preferably greater than 61° C., preferably greater than 62° C., preferably greater than 63° C., preferably greater than 64° C., preferably greater than 65° C., and preferably less than 66° C., preferably less than 65° C., preferably less than 64° C., preferably less than 63° C., preferably less than 62° C., preferably less than 61° C., preferably less than 60° C., preferably less than 59° C., preferably less than 58° C., preferably less than 57° C., preferably less than 56° C., preferably less than 55° C., preferably less than 54° C., preferably less than 53° C., preferably less than 52° C., preferably less than 51° C., preferably less than 50° C., preferably less than 49° C., preferably less than 48° C., preferably less than 47° C., preferably less than 46° C.

In another embodiment of the present invention, the photosensitizers suitable for use in the present invention are selected from the group consisting of porphyrins, metalloporphyrins, porphins, chlorophylls, purpurins, fluoresceins, phthalocyanines, metal phthalocyanines, indocyanine green, tricarbocyanines, nanogold particles, metal nanoparticles, metal oxide nanoparticles, metal sulfides nanoparticles, metal carbide nanoparticles, carbon nanotubes, graphene, and the like, as well as derivatives of the foregoing compounds, or degradation products of the foregoing compounds, or salt forms of the foregoing compounds. In a preferred embodiment, the photosensitizer is selected from the group consisting of indole monocyanine (monomethine cyanine), indole carbocyanine (trimethine cyanine), indole dicarbocyanine (pentamethine cyanine), indole tricarbocyanine (heptamethine cyanine), tricarbocyanine dyes, benzoindole semicyanine dyes, indole squarylium dyes, phthalocyanines, chlorophyll derivatives, pheophytin, pheophorbide a and its derivatives, dihydroporphine e6 and its derivatives, purpurin 18, dihydroporphine p6 and its derivatives, dihydroporphine e4 and its derivatives, dihydroporphine f and its derivatives, protoporphyrin and its derivatives, benzochloroporphyrins, metalloporphyrins, hematoporphyrin derivatives (HpD), porfimer sodium, photocarcinorin (PSD-007), nanogold, nanotungsten oxides, nano-Cu sulfides, nano-Fe-oxides, nano-nickel carbide, nano-molybdenum oxide, and other water-soluble or fat-soluble derivatives based on the modification of the above photosensitizers.

In another embodiment of the present invention, the photosensitizer may be a photosensitizer with an activation wavelength range of 400-600 nm of an laser light source, such as fluorescein; the photosensitizer may be a photosensitizer with an activation wavelength range of 600-750 nm of an laser light source, such as purpurin 18; the photosensitizers may be photosensitizers with an activation wavelength range of 700 to 900 nm of an laser light source, such as Indocyanine Green ICG; the photosensitizers may be photosensitizers with an activation wavelength range of 800 to 1100 nm of an laser light source, such as nanogold.

In another embodiment of the present invention, the fluorescent agent and/or the photosensitizer contains a reactive group in the molecular structure, such as: hydroxyl, thiol, amino, imino, carboxyl, acid anhydride, aldehyde, isocyanate, siloxane group, epoxy, cyclic nitrogenous group, etc., and can react with the groups on the molecular side chains of the copolymer material; the photosensitizer molecules are covalently bonded to the molecular chains of the copolymer materials, and the photosensitizer is fixed inside or on the surface of the copolymer material, and cannot freely enter the blood or other body fluids.

In one embodiment of the present invention, when the fluorescent agent and/or photosensitizer contains a polymerizable group in the molecular structure, for example: vinyl, allyl, butenyl, acryloyloxy, methacryloyloxy, acrylamido, methacrylamido, vinyl ether group, alkynyl, hydroxy, mercapto, amino, imino, carboxyl, acid anhydride, aldehyde group, isocyanate group, siloxane group, epoxy, cyclic nitrogenous group, etc., the copolymerization may occur with the polymerizable monomers of the copolymer material. The fluorescent agent and/or photosensitizer molecules are present in the molecular chain of the copolymer material in the form of covalent bonds. The fluorescent agent and/or photosensitizer is fixed on the copolymer material. Therefore, the toxicity of the fluorescent agent and/or the photosensitizer itself can be completely ignored.

In another embodiment of the present invention, when the fluorescent agent and/or photosensitizer is dispersed in the copolymer material by way of blending or doping, the fluorescent agent and/or photosensitizer molecule is bonded to the molecular chain of the copolymer material by hydrogen bond or the van der Waals forces, and the fluorescent agent and/or photosensitizer molecules are bound to the copolymer material and cannot freely enter the blood or other body fluids.

In another embodiment of the present invention, when the fluorescent agent and/or photosensitizer is fixed on the surface of the copolymer material by surface grafting and/or surface modification, the copolymer material is selected from the group consisting of polymerizable copolymer materials, preferably contains well biocompatible polymerizable groups on the surface, such as: vinyl, allyl, butenyl, acryloyloxy, methacryloyloxy, acrylamido, methacrylamido, vinyl ether group, alkynyl, hydroxyl, thiol, amino, imino, carboxyl, anhydride, aldehyde group, isocyanate group, siloxane group, epoxy, cyclic nitrogenous group, etc., wherein the fluorescent agent and/or photosensitizer can undergo grafting reaction with the copolymer material, the copolymer material is combined with the fluorescent agent and/or the photosensitizer molecule in the form of a covalent bond, and the fluorescent agent and/or the photosensitizer is fixed inside or on the surface of the copolymer material, and cannot freely enter the blood or other body fluids.

In another preferred embodiment, the fluorescent agent and/or photosensitizer is dispersed in other auxiliary agents (e.g., co-solvents, emulsifiers, lubricants, hydrophilic coatings, drug loading, color masterbatch, UV absorbents, cross-linking agent, coupling agents, pH regulators, antistatic agents, release agents etc.) by dissolving, suspending, emulsifying, and the like, and coated on the surface of the copolymer material, the fluorescent agent and/or photosensitizer molecule is bonded to the molecular chain of the copolymer material by hydrogen bond or the van der Waals forces, and the fluorescent agent and/or photosensitizer molecules are bound to the surface of the copolymer material and cannot freely enter the blood or other body fluids.

In another preferred embodiment, in order to enhance the affinity between the fluorescent agent and/or photosensitizer molecule with the copolymer material molecule, the fluorescent agent and/or photosensitizer molecule can be chemically modified without changing the photoactivity; the copolymer material may also be subjected to activation treatment including, but not limited to, plasma treatment, corona treatment, flame treatment, strong acid treatment, strong alkali treatment, and the like.

Other polymerizable monomers that can be used in the present invention include: butadiene, styrene, alpha-methyl styrene, sodium styrene sulfonate, vinyl toluene, acrylonitrile, methacrylonitrile, alpha-chloro-acrylonitrile, ethylacrylonitrile, methyl vinyl ether, isopropyl vinyl ether, n-butyl vinyl ether, isobutyl vinyl ether, tert-butyl vinyl ether, 2-ethylhexyl vinyl ether, 4-hydroxybutyl vinyl ether, 1,4-butanediol divinyl ether, diethylene glycol divinyl ether, vinyl esters such as vinyl acetate, vinyl alkoxycarboxylate, vinyl propionate, vinyl butyrate, vinyl isobutyrate, vinyl caproate, vinyl 2-ethylhexanoate, and vinyl caprate; allyl chloride, methallyl chloride, dichloroethylene, vinyl chloride, vinyl fluoride, difluoroethylene, sodium vinyl sulfonate, butyl vinyl sulfonate, phenyl vinyl sulfone, methyl vinyl sulfone, N-vinyl pyrrolidine dione, N-ethylene oxazolidinedione, acrolein, acrylamide, methacrylamide, N,N-dimethyl(meth)acrylamide, methylol acrylamide, N-butoxy (meth)acrylamide, isobutoxy(meth)acrylamide, etc.; other ethylenically unsaturated carboxylic acids and esters thereof, such as dialkyl or trialkyl esters of dibasic and tribasic carboxylic acids, including di(2-ethylhexyl) maleate, dibutyl maleate, dimethyl fumarate, dimethyl itaconate, diethyl citraconicate, trimethyl aconiate, diethyl mesaconate, di(2-ethylhexyl) itaconate, di(2-chloroethyl) itaconate, maleic acid, maleic anhydride, fumaric acid, itaconic acid; and olefins such as diisobutylene, 1-octene, 1-decene, 1-hexadecene, and the like, or mixtures thereof.

In one embodiment of the present invention, when the fluorescent agent and/or photosensitizer are polymerized with the copolymer material to obtain the material of the invention, or when the fluorescent agent and/or the photosensitizer is dispersed in the copolymer material to obtain the material of the invention, the material of the invention can be prepared by a method that includes the following steps:
 1) mixing polymerizable monomers with optional additives such as thermal crosslinking agent, initiators, UV absorbents, and the like;
 2) adding fluorescent agent and/or photosensitizer and dissolving it, then conducting the polymerization.

More specifically, the material of the present invention can be prepared by a method comprising the following steps:
 1) mixing polymerizable monomers with thermal initiators, crosslinking agent and/or UV absorbents;
 2) adding a fluorescent agent and/or a photosensitizer to dissolve it;
 3) placing the reaction system obtained in 2) in a mold;
 4) conducting the polymerization, such as water bath polymerization;
 5) conducting the polymerization again in the dryer.

In another embodiment of the present invention, when the fluorescent agent and/or the photosensitizer is fixed on the surface of the copolymer material by surface grafting or surface modification, the material of the present invention can be prepared by a method comprising the following steps:
 1) mixing polymerizable monomers with optional additives such as a cross-linking agent, a thermal initiator, an ultraviolet absorbent, etc., and then polymerizing to obtain a copolymer material;
 2) adding a fluorescent agent and/or a photosensitizer, and dissolving it, for example, dissolving the fluorescent agent and/or photosensitizer with a suitable adjuvant (e.g., polymerizable monomers), followed by polymerization such as graft polymerization or surface modification or transfer printing.

More specifically, the material of the present invention can be prepared by a method comprising the following steps:
 1) mixing polymerizable monomers with thermal initiator, crosslinking agent and/or UV absorbent;
 2) transferring the reaction system obtained in 1) to a mold;
 4) conducting the polymerization, such as water bath polymerization;
 5) conducting polymerization again in the dryer;
 6) dissolving fluorescent agent and/or photosensitizer, for example, dissolving the fluorescent agent and/or photosensitizer with a suitable polymerizable monomer;
 7) conducting the polymerization of the above-obtained system again, such as graft polymerization or surface modification or transfer printing.

In another embodiment of the present invention, when the fluorescent agent and/or the photosensitizer is fixed on the surface of the copolymer material by surface-coating mode, the material of the present invention can be prepared by a method comprising the following steps:
 1) obtaining a suitable copolymer material;
 2) fluorescent agent and/or photosensitizer, for example the fluorescent agent and/or photosensitizer dissolved with a suitable solvent, coated on the surface of the copolymer material.

The material of the present invention can be used for manufacturing medical treatment devices and medical detection devices such as intraocular lens, and can also be used to manufacture corneal contact lens, orthokeratology lens, iris hook, eye endoscope, artificial cornea, corneal inner ring, capsular bag tension ring, intracorneal lens, glaucoma drainage valve, drug sustained-release carrier, intraocular filler, fundus filler, glasses, goggles, lenses for medical devices, or when it contains therapeutics and/or photosensitizers, it can be used to make medical treatments devices (such as devices for treating ophthalmic diseases), such as devices for treating after-cataract (such as intraocular lens for treating after-cataract), or when it contains fluorescent agents, it can be used to manufacture medical detection devices (so that the resulting articles can be used for detection by virtue of the fluorescent properties, in particular, ophthalmic devices, such as lenses with fluorescent properties, in particular ophthalmic lenses, intraocular lens with fluorescence properties, corneal contact lens, orthokeratology lens, iris hooks, intraocular lens, artificial corneas, corneal inner ring, capsular bag tension ring, intracorneal lens, glaucoma drainage valve, drug sustained-release carrier, intraocular filler, fundus filler, glasses, goggles, lenses for medical devices, telescopes, observation mirrors, etc.) or other ophthalmic equipment or consumables.

The invention also relates to the use of the material of the invention in the preparation of the above devices or equipment (such as a medical treatment device, a medical detection device), such as an intraocular lens, corneal contact lens, orthokeratology lens, iris hooks, intraocular lens, artificial corneas, corneal inner ring, capsular bag tension ring, intracorneal lens, glaucoma drainage valve, drug sustained-release carrier, intraocular filler, fundus filler, glasses, goggles, lenses for medical devices or when it contains therapeutic agents and/or photosensitizers, it can be used for manufacturing a medical treatment device (such as a device for treating ophthalmic diseases), such as devices for treating after-cataract, or when it contains fluorescent agents, it can be used to manufacture medical detection devices (so that the resulting articles can be used for detection by virtue of the fluorescent properties, in particular, ophthalmic devices, such as lenses with fluorescent properties, in particular ophthalmic lenses, intraocular lens with fluorescence properties, corneal contact lens, orthokeratology lens, iris hooks, intraocular lens, artificial corneas, corneal inner ring, capsular bag tension ring, intracorneal lens, glaucoma drainage valve, drug sustained-release carrier, intraocular filler, fundus filler, glasses, goggles, lenses for medical devices, telescopes, observation mirrors, etc.) or other ophthalmic equipment or consumables.

As used herein, the term "alkyl" means linear or branched hydrocarbons having 1 to 500 carbon atoms, or 1 to 100 carbon atoms, or 1 to 50 carbon atoms, or 1 to 20 carbon atoms, or 1 to 10 carbon atoms, or 1 to 8 carbon atoms, 1 to 6 carbon atoms, 1 to 4 carbon atoms, or 1 to 3 carbon atoms, unless otherwise specified. Representative examples of alkyl include, but are not limited to, methyl, ethyl, n-propyl, isopropyl, n-butyl, sec-butyl, isobutyl, tert-butyl, n-pentyl, isopentyl, neo-pentyl, n-hexyl, 3-methylhexyl, 2,2-dimethylpentyl, 2,3-dimethylpentyl, n-heptyl, n-octyl, n-nonyl, and n-decyl, undecyl lauryl, tridecyl, tetradecyl, pentadecyl, hexadecyl, heptadecyl, octadecyl, nonadecyl, eicosyl. When the "alkyl" group is a linker between two other moieties, it may also be linear or branched; examples include but are not limited to —$CH_2$—, —$CH_2CH_2$—, —$CH_2CH_2CH(CH_3)$—, —$CH_2CH(CH_2CH_3)CH_2$—.

As used herein, the term "aryl" refers to a phenyl group (i.e., a monocyclic aryl group) or a bicyclic system containing at least one benzene ring or an aromatic bicycle containing only carbon atoms in an aromatic bicyclic system. The bicyclic aryl may be azulenyl, naphthyl, or phenyl fused to a monocyclic cycloalkyl, monocyclic cycloalkenyl, or monocyclic heterocyclyl. The bicyclic aryl group is attached to the parent molecular moiety through any carbon atom contained within the phenyl moiety of the bicyclic system or any carbon atom of a naphthyl or fluorenyl ring. The fused monocyclic cycloalkyl or monocyclic heterocyclyl moiety of the bicyclic aryl is optionally substituted with one or two oxo and/or thiohetero groups. Representative examples of bicyclic aryl include, but are not limited to, azulenyl, naphthyl, indan-1-yl, indan-2-yl, indan-3-yl, indan-4-yl, 2,3-dihydroindol-4-yl, 2,3-dihydroindol-5-yl, 2,3-dihydroindol-6-yl, 2,3-dihydroindol-7-yl, inden-1-yl, inden-2-yl, inden-3-yl, inden-4-yl, dihydronaphthalen-2-yl, dihydronaphthalen-3-yl, dihydronaphthyl-4-yl, dihydronaphth-1-yl, 5,6,7,8-tetrahydronaphthalen-1-yl, 5,6,7,8-tetrahydronaphthalen-2-yl, 2,3-dihydrobenzofuran-4-yl, 2,3-dihydrobenzofuran-5-yl, 2,3-dihydrobenzofuran-6-yl, 2,3-dihydrobenzofuran-7-yl, benzo[d][1,3]dioxol-4-yl, benzo[d][1,3]dioxol-5-yl, 2H-chromen-2-one-5-yl, 2H-chromen-2-one-6-yl, 2H-chromen-2-one-7-yl, 2H-chromen-2-one-8-yl, isoindoline-1,3-dione-4-yl, isoindoline-1,3-dione-5-yl, inden-1-one-4-yl, inden-1-one-5-yl, inden-1-one-6-yl, inden-1-one-7-yl, 2,3-dihydrobenzo[b][1,4]dioxan-5-yl, 2,3-dihydrobenzo[b][1,4]dioxan-6-yl, 2H-benzo[b][1,4]oxazine3(4H)-one-5-yl, 2H-benzo[b][1,4]oxazine3(4H)-one-6-yl, 2H-benzo[b][1,4]oxazine3(4H)-one-7-yl, 2H-benzo[b][1,4]oxazine3(4H)-one-8-yl, benzo[d]oxazine-2(3H)-one-5-yl, benzo[d]oxazine-2(3H)-one-6-yl, benzo[d]oxazine-2(3H)-one-7-yl, benzo[d]oxazine-2(3H)-one-8-yl, quinazoline-4(3H)-one-5-yl, quinazoline-4(3H)-one-6-yl, quinazoline-4(3H)-one-7-yl, quinazoline-4(3H)-one-8-yl, quinoxaline-2(1H)-one-5-yl, quinoxalin-2(1H)-one-6-yl, quinoxalin-2(1H)-one-7-yl, quinoxaline-2(1H)-one-8-yl, benzo[d]thiazol-2(3H)-one-4-yl, benzo[d]thiazol-2(3H)-one-5-yl, benzo[d]thiazole-2(3H)-one-6-yl and benzo[d]thiazol-2(3H)-one-7-yl. In certain embodiments, the bicyclic aryl is fused to a 5- or 6-membered monocyclic cycloalkyl, a 5- or 6-membered monocyclic cycloalkenyl, or (i) a naphthyl group or (ii) phenyl rings of a 5- or 6-membered monocyclic heterocyclyl, wherein the fused cycloalkyl, cycloalkenyl and heterocyclyl groups are optionally substituted with one or two groups which are independently oxo or thia.

The term "arylalkyl," or "alkylaryl," as used herein, refers to an aryl group, as defined herein, bonded to the parent molecular moiety through an alkyl group, as defined herein. Representative examples of arylalkyl include, but are not limited to, benzyl, 2-phenylethyl, 3-phenylpropyl, and 2-naphthalen-2-ylethyl.

The term "cycloalkyl" as used herein refers to a monocyclic or bicyclic cycloalkyl ring system. Monocyclic systems are cyclic hydrocarbon groups containing 3 to 8 carbon atoms, wherein such groups may be saturated or unsaturated but not aromatic. In certain embodiments, the cycloalkyl group is fully saturated. Examples of monocyclic cycloalkyls include cyclopropyl, cyclobutyl, cyclopentyl, cyclopentenyl, cyclohexyl, cyclohexenyl, cycloheptyl and cyclooctyl. Bicyclic cycloalkyl ring systems are bridged monocyclic or fused bicycles. A bridged monocycle contains a monocyclic cycloalkyl ring in which two non-adjacent carbon atoms of the single ring are connected by an alkylene bridge of one to three additional carbon atoms (i.e., the bridging group of —$(CH_2)_w$— form, wherein w is 1, 2 or 3). Representative examples of bicyclic systems include, but are not limited to, bicyclo[3.1.1]heptane, bicyclo[2.2.1]heptane, bicyclo[2.2.2]octane, bicyclo[3.2.2]nonane, bicyclo[3.3.1]nonane and bicyclo[4.2.1]nonane. Fused bicyclic cycloalkyl ring systems contain a monocyclic cycloalkyl ring fused to a phenyl, a monocyclic cycloalkyl, a monocyclic cycloalkenyl, a monocyclic heterocyclyl, or a monocyclic heteroaryl. A bridged or fused bicyclic cycloalkyl group is attached to the parent molecular moiety through any carbon atom contained within the monocyclic cycloalkyl ring. Cycloalkyl groups are optionally substituted with one or two groups that are independently oxo or thia. In certain embodiments, the fused bicyclic cycloalkyl is 5- or 6-membered monocyclic cycloalkyl ring fused to a phenyl ring, a 5- or 6-membered monocyclic cycloalkyl, a 5- or 6-membered monocyclic cycloalkenyl, a 5- or 6-membered monocyclic heterocycle group, or a 5- or 6-membered monocyclic heteroaryl, wherein the fused bicyclic cycloalkyl is optionally substituted with one or two groups which are independently oxo or thia.

The term "heteroaryl" as used herein refers to a monocyclic heteroaryl or bicyclic system containing at least one heteroaromatic ring. The monocyclic heteroaryl may be a 5- or 6-membered ring. The 5-membered ring consists of two double bonds and one, two, three or four nitrogen atoms and optionally one oxygen or sulfur atom. The 6-membered ring consists of three double bonds and one, two, three or four nitrogen atoms. The 5- or 6-membered heteroaryl is attached to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridyl, pyridazinyl, pyrimidinyl, pyrazinyl, pyrazolyl, pyrrolyl, tetrazolyl, thiadiazolyl, thiazolyl, thienyl, triazolyl and triazinyl. Bicyclic heteroaryl groups consist of monocyclic heteroaryl groups fused to phenyl, monocyclic cycloalkyl, monocyclic cycloalkenyl, monocyclic heterocyclyl or monocyclic heteroaryl. The fused cycloalkyl or heterocyclyl portion of the bicyclic heteroaryl group is optionally substituted with one or two groups that are independently oxo or thia. When the bicyclic heteroaryl contains a fused cycloalkyl, cycloalkenyl, or heterocyclyl ring, then the bicyclic heteroaryl group is attached to the parent molecule moiety via any carbon or nitrogen atom contained within the monocyclic heteroaryl portion of the bicyclic system. When the bicyclic heteroaryl is a monocyclic heteroaryl fused to a phenyl ring, the bicyclic heteroaryl group is attached to the parent molecular moiety through any carbon or nitrogen atom within the bicyclic system. Representative examples of bicyclic heteroaryl include, but are not limited to, benzimidazolyl, benzofuranyl, benzothienyl, benzoxadiazolyl, benzoxathiathiadiazolyl, benzothiazolyl, cinnolinyl, 5,6-dihydroquinolin-2-yl, 5,6-dihydroisoquinolin-1-yl, furanopyridinyl, indazolyl, indolyl, isoquinolinyl, naphthyridyl, quinolinyl, purinyl, 5,6,7,8-tetrahydroquinolin-2-yl, 5,6,7,8-tetrahydroquinoline-3-yl, 5,6,7,8-tetrahydroquinolin-4-yl, 5,6,7,8-tetrahydroisoquinolin-1-yl, thienopyridinyl, 4,5,6,7-tetrahydrobenzo[c][1,2,5]oxadiazolyl and 6,7-dihydrobenzo[c][1,2,5]oxadiazol-4(5H)-one. In certain embodiments, the fused bicyclic heteroaryl is fused to a phenyl ring, a 5- or 6-membered monocyclic cycloalkyl, a 5- or 6-membered monocyclic cycloalkenyl, a 5- or 6-membered monocyclic heterocycle group, or 5- or 6-membered monocyclic heteroaryl ring of a 5- or 6-membered monocyclic heteroaryl, wherein the fused cycloalkyl, cycloalkenyl and heterocyclyl radicals are optionally substituted with one or two groups which are independently oxo or thia.

The terms "heteroarylalkyl" and "-alkylheteroaryl" as used herein, refer to a heteroaryl group, as defined herein, linked to the parent molecular moiety through an alkyl group, as defined herein. Representative examples of heteroarylalkyl include, but are not limited to, furan-3-ylmethyl, 1H-imidazol-2-ylmethyl, 1H-imidazol-4-ylmethyl, 1-(pyridin-4-yl)-ethyl, pyridin-3-ylmethyl, pyridin-4-ylmethyl, pyrimidin-5-ylmethyl, 2-(pyrimidin-2-yl)propyl, thiophen-2-ylmethyl and thiophene-3-yl methyl group.

The term "heterocyclyl," as used herein, refers to a monocyclic heterocycle or a bicyclic heterocycle. Monocyclic heterocycles are 3, 4, 5, 6 or 7 membered rings containing at least one heteroatom independently selected from O, N, and S, wherein the ring is saturated or unsaturated but not aromatic. The 3- or 4-membered ring contains 1 heteroatom selected from O, N, and S. The 5-membered ring may contain zero or one double bond and one, two, or three heteroatoms selected from O, N, and S. The 6- or 7-membered ring contains zero, one, or two double bonds and one, two, or three heteroatoms selected from O, N, and S. The monocyclic heterocycle is attached to the parent molecular moiety through any carbon atom or any nitrogen atom contained within the monocyclic heterocycle. Representative examples of monocyclic heterocyclic rings include, but are not limited to, azetidinyl, azepanyl, aziridinyl, diazepanyl, 1,3-dioxanyl, 1,3-dioxocyclopentyl, 1,3-dithiacyclopentyl, 1,3-dithianyl, imidazolinyl, imidazolidinyl, isothiazolinyl, isothiazolidinyl, isooxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothiophenyl, thiadiazolinyl, thiadiazolidinyl, thiazolinyl, thiazolidinyl, thiomorpholinyl 1,1-dioxidethiomorpholinyl (thiomorpholinylsulfone), thiopyranyl, and trithianyl. Bicyclic heterocycles are monocyclic heterocycles fused to phenyl, monocyclic cycloalkyl, monocyclic cycloalkenyl, monocyclic heterocycle, or monocyclic heteroaryl. The bicyclic heterocycle is attached to the parent molecular moiety through any carbon atom or any nitrogen atom contained within the monocyclic heterocycle portion of the bicyclic system. Representative examples of bicyclic heterocyclyl include, but are not limited to, 2,3-dihydrobenzofuran-2-yl, 2,3-dihydrobenzofuran-3-yl, indan-1-yl, indan-2-yl, indan-3-yl, 2,3-dihydrobenzothiophen-2-yl, decahydroquinolinyl, decahydroisoquinolinyl, octahydro-1H-indoyl and octahydrobenzofuranyl. The heterocyclic group is optionally substituted with one or two groups that are independently oxo or thia. In certain embodiments, the bicyclic heterocyclic group is fused to a phenyl ring, a 5- or 6-membered monocyclic cycloalkyl, a 5- or 6-membered monocyclic cycloalkenyl, a 5- or 6-membered monocyclic heterocyclyl, or a 5 or 6-membered monocyclic heteroaryl ring of 5 or 6-membered monocyclic heterocyclyl, wherein the bicyclic heterocyclyl is optionally substituted with one or two groups which are independently oxo or thia.

Example

Hereinafter, the present invention will be described in more detail by means of specific examples, but the examples provided are only illustrative and not intended to limit the present invention.

Examples 1-26 shown in Table 1 illustrate the materials of the present invention. All the examples in Table 1 were prepared in the following manner and all the monomers were purified by distillation under reduced pressure. In a 250-ml beaker, all the required monomers were mixed in respective proportions, initiators and light absorbents were added, stirred well and filtered, and transferred to a special mold. The various vessels and molds used in the above-mentioned implementation process were cleaned, dried and sterilized before use.

Nitrogen was blown into the monomer solution in the mold, and the mold was sealed under nitrogen protection. The mold was then placed in a water bath at a set temperature for polymerization for at least 24 hours, and then the mold was transferred to an oven at set temperature to keep temperature for 24 hours (Note: the set temperature of the oven should be higher than the set temperature of the water bath). The polymer molded in the mold was taken out and then naturally cooled to room temperature, or it is cut into pieces of a desired size and shape while hot, and extracted with an alcoholic solvent at a certain temperature for at least 24 hours to remove residual small molecules. Finally, the blank was placed in a vacuum oven at a set temperature and dried overnight to obtain the material of the invention.

TABLE 1

Examples 1 to 26

| Example | HEMA | HEA | EOEMA | EOEOEA | POEA | PEA | PEMA | BMA | MMA | EMA | EA | BA | Y28 | RI | Water % | $T_g$/°C |
|---|---|---|---|---|---|---|---|---|---|---|---|---|---|---|---|---|
| 1 | 30 | | | | 40 | | | | | | 26 | | | 1.5077 | 5.2 | 23.0 |
| 2 | 30 | | | | 50 | | | | | | 16 | | | 1.5295 | 5.0 | 26.1 |
| 3 | | 26 | | | | | 40 | | | | | 30 | | 1.5242 | 5.4 | 21.1 |
| 4 | | 40 | | | | | 40 | | | | | 16 | | 1.5204 | 6.1 | 27.9 |
| 5 | 40 | | | | 30 | | | | | | 26 | | | 1.5040 | 7.7 | 24.2 |
| 6 | 40 | | | | 40 | | | | | | 16 | | | 1.5100 | 7.0 | 26.9 |
| 7 | 20 | | 20 | | | 30 | 26 | | | | | | | 1.5369 | 7.2 | 26.2 |
| 8 | 20 | | | 20 | | 26 | 30 | | | | | | | 1.5377 | 7.6 | 24.6 |
| 9 | | 26 | 20 | | 30 | | | 20 | | | | | | 1.5295 | 12.1 | 11.2 |
| 10 | | 20 | | 20 | 20 | | | | 36 | | | | | 1.5380 | 8.2 | 20.4 |
| 11 | 40 | | | | 50 | | | | | 6 | | | | 1.5178 | 7.0 | 28.2 |
| 12 | | 30 | | | | 20 | 30 | | | 16 | | | | 1.5326 | 5.3 | 24.0 |
| 13 | | 30 | | 30 | | | 36 | | | | | | | 1.5157 | 13.2 | 10.4 |
| 14 | 50 | | | | 20 | | | | | | 26 | | | 1.4924 | 9.6 | 35.0 |
| 15 | | 30 | | | | | | 40 | | | 26 | | | 1.5121 | 5.3 | 21.0 |
| 16 | | 40 | | | | | | 40 | | | 16 | | | 1.5103 | 8.1 | 23.9 |
| 17 | 30 | | | | 60 | | | | | 6 | | | | 1.5360 | 5.0 | 28.0 |
| 18 | 40 | | | | 20 | | | | | | 36 | | | 1.4985 | 7.8 | 20.1 |
| 19 | | 40 | | | 40 | | | | 16 | | | | | 1.5149 | 7.4 | 26.4 |
| 20 | | 40 | | | 40 | | | | | 16 | | | | 1.5128 | 7.6 | 25.0 |
| 21 | 30 | | | | 50 | | | | | | 16 | | 0.03 | 1.5038 | 5.1 | 25.9 |
| 22 | 40 | | | | 30 | | | | | | 26 | | 0.03 | 1.5293 | 7.6 | 24.1 |
| 23 | | 30 | | | | 20 | 30 | | | 16 | | | 0.03 | 1.5333 | 5.4 | 24.1 |
| 24 | | 30 | | | | 20 | 30 | | 16 | | | | 0.03 | 1.5353 | 5.2 | 24.5 |
| 25 | 50 | | 26 | | | 20 | | | | | | | 0.03 | 1.4903 | 14.7 | 25.2 |
| 26 | | 30 | | | | | | 40 | | | 26 | | 0.03 | 1.5128 | 5.2 | 21.2 |

MMA: methyl methacrylate
EA: ethyl acrylate
EMA: ethyl methacrylate
BA: butyl acrylate
HEMA: hydroxyethyl methacrylate
HEA: hydroxyethyl acrylate
PEA: phenylethyl acrylate
PEMA: phenylethyl methacrylate
POEA: phenoxyethyl acrylate
BMA: benzylethyl methacrylate
EOEMA: ethoxyethyl methacrylate
EOEOEA: ethoxyethoxyethyl acrylate
Y28: blue light absorbent
RI: refractive index value after hydration measured at 35° C.
Water %: water content
Tg: glass transition temperature of materials (dry state)

Example 27: Preparation of Intraocular Lens

The intraocular lens was processed with the prepared material: the material is turned at room temperature to divide the prepared polymer material into a IOL billet having a thickness of about 3 mm and a diameter of about 16 mm, and then turned on a single-point diamond lathe (OPTOFORM) to shape. After shaping, the intraocular lens was polished by the polishing medium, and the surface was cleaned and hydrated by rinsing into physiological saline to obtain a water-absorbing balance, and the intraocular lens was obtained. The resulting intraocular lens was stored in sterile physiological saline.

Figure 1:
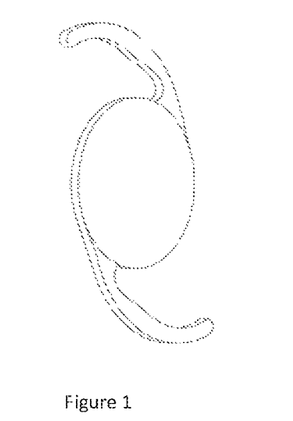
FIG. 1 illustrates an embodiment of an intraocular lens with the body's edge directly attached to the haptics.
Figure 2:
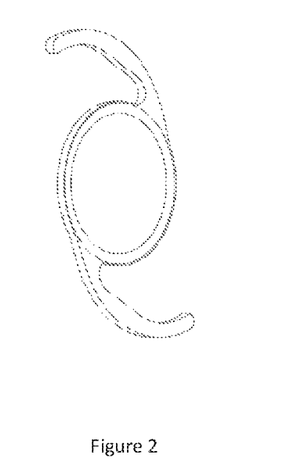
FIG. 2 illustrates another embodiment of an intraocular lens using a modified "L" haptics shape.

Table 2 shows schematically some of the examples of the intraocular lens prepared by the partial material of the present invention. The parameters involved in the table include: D-IOL diopter in the human eye; n—refractive index; CT—intraocular lens center thickness; Ra—radius of curvature of the front surface (the surface of the IOL farther from the retina); Rp—the radius of curvature of the rear surface (the surface of the IOL closer to the retina); and ET—the edge thickness of the IOL optic zone. In this example, the diameter of the main body of the intraocular lens is 6.0 mm, the total diameter is 13.0 mm, and the thickness of the haptics is 0.34 mm. In this example, the diameter of the main body of the intraocular lens is 6.0 mm. When the diameter of the optical zone is equal to the diameter of the main body, the outer periphery of the main body of the intraocular lens has no flange change and is directly connected with the haptics. For example, in Run 1, the radius of the optical zone is equal to the radius of the main body, and the edge thickness of the optical zone≥the thickness of haptics, then the main body edge is directly connected with haptics, as shown in FIG. 1; when the diameter of the optical zone<the diameter of the main body, such as Runs 3, 5, 6 and so on. The edge thickness of the optical zone is gradually increased to the thickness of the crucible by flanging the edge, as shown in FIG. 2. In the example, the intraocular lens adopts a modified "L" haptics shape with a total diameter of 13.0 mm, and the optical part adopts an equal bi-convex structure. The front and rear surfaces of the intraocular lens have a spherical design as an example.

Runs 1-30 only schematically shows that the intraocular lens prepared using the material of the present invention can maintain a thinner thickness and a smaller overall volume of the intraocular lens, facilitating the passage through smaller incisions, any of which is based on these embodiments. All the modifications, as long as they meet the spirit and scope of the present invention, will fall within the scope of the present invention. For example, those skilled in the art can conceive, according to the examples of the present invention, that the intraocular lens can be other types of haptics shape such as C-type haptics, plate type haptics, etc.; the total length of the intraocular lens and the size of the optical zone can be varied according to different applications and requirements; the shape of the optical surface is not limited to a biconvex spherical surface, it may be of unequal convex shape, and may also be attached with different functional optical surfaces such as toric, refractive multifocal/diffractive multifocal surface, aspherical surface or any combination of optical surfaces.

TABLE 2

Example of Intraocular Lens Prepared by Materials of the Present Invention

| Run | D | n | CT | Ra | Rp | ET |
|---|---|---|---|---|---|---|
| 1 | 6.00 | 1.5077 | 0.50 | 57.205 | −57.205 | 0.343 |
| 2 | 20.00 | 1.5077 | 0.70 | 17.130 | −17.130 | 0.171 |
| 3 | 30.00 | 1.5077 | 0.80 | 11.401 | −11.401 | 0.199 |
| 4 | 6.00 | 1.5295 | 0.48 | 64.470 | −64.470 | 0.340 |
| 5 | 20.00 | 1.5295 | 0.69 | 19.306 | −19.306 | 0.338 |
| 6 | 36.00 | 1.5295 | 0.80 | 10.699 | −10.699 | 0.208 |
| 7 | 6.00 | 1.5360 | 0.47 | 66.636 | −66.636 | 0.335 |
| 8 | 20.00 | 1.5360 | 0.69 | 19.955 | −19.955 | 0.350 |
| 9 | 36.00 | 1.5360 | 0.72 | 11.064 | −11.064 | 0.148 |
| 10 | 6.00 | 1.4985 | 0.48 | 54.141 | −54.141 | 0.314 |
| 11 | 20.00 | 1.4985 | 0.69 | 16.213 | −16.213 | 0.270 |
| 12 | 30.00 | 1.4985 | 0.72 | 10.794 | −10.794 | 0.133 |
| 13 | 6.00 | 1.5040 | 0.50 | 55.972 | −55.972 | 0.339 |
| 14 | 20.00 | 1.5040 | 0.69 | 16.761 | −16.761 | 0.284 |
| 15 | 30.00 | 1.5040 | 0.72 | 11.160 | −11.160 | 0.153 |
| 16 | 6.00 | 1.5100 | 0.50 | 57.971 | −57.971 | 0.345 |
| 17 | 20.00 | 1.5100 | 0.69 | 17.360 | −17.360 | 0.202 |
| 18 | 30.00 | 1.5100 | 0.72 | 11.558 | −11.558 | 0.173 |
| 19 | 6.00 | 1.5178 | 0.50 | 60.570 | −60.570 | 0.351 |
| 20 | 20.00 | 1.5178 | 0.69 | 18.139 | −18.139 | 0.344 |
| 21 | 30.00 | 1.5178 | 0.72 | 12.077 | −12.077 | 0.197 |
| 22 | 6.00 | 1.5038 | 0.51 | 55.905 | −55.905 | 0.349 |
| 23 | 20.00 | 1.5038 | 0.69 | 16.741 | −16.741 | 0.184 |
| 24 | 30.00 | 1.5038 | 0.74 | 11.145 | −11.145 | 0.172 |
| 25 | 6.00 | 1.5293 | 0.48 | 64.403 | −64.403 | 0.340 |
| 26 | 20.00 | 1.5293 | 0.64 | 19.289 | −19.289 | 0.202 |
| 27 | 36.00 | 1.5293 | 0.76 | 10.691 | −10.691 | 0.167 |
| 28 | 6.00 | 1.4924 | 0.51 | 52.107 | −52.107 | 0.337 |
| 29 | 20.00 | 1.4924 | 0.68 | 15.604 | −15.604 | 0.173 |
| 30 | 30.00 | 1.4924 | 0.78 | 10.386 | −10.386 | 0.169 |

Example 28: Spectral Transmittance of an Intraocular Lens Made of the Material

Figure 3:
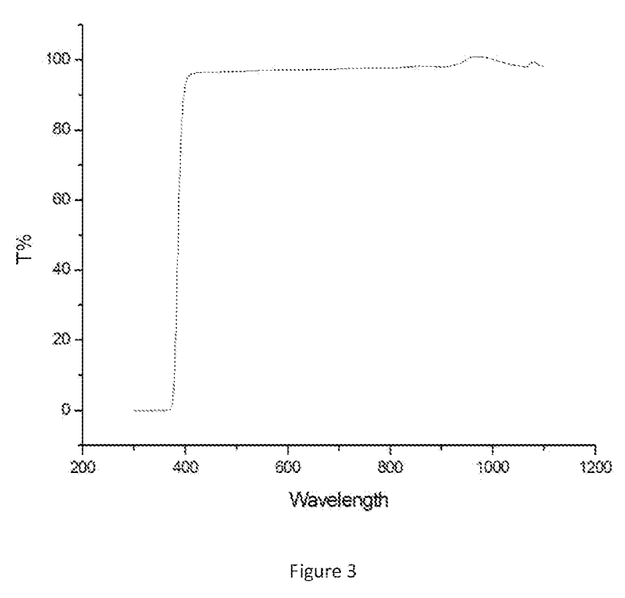
FIG. 3 illustrates the spectral transmittance curve of a specific Example 6.
Figure 4:
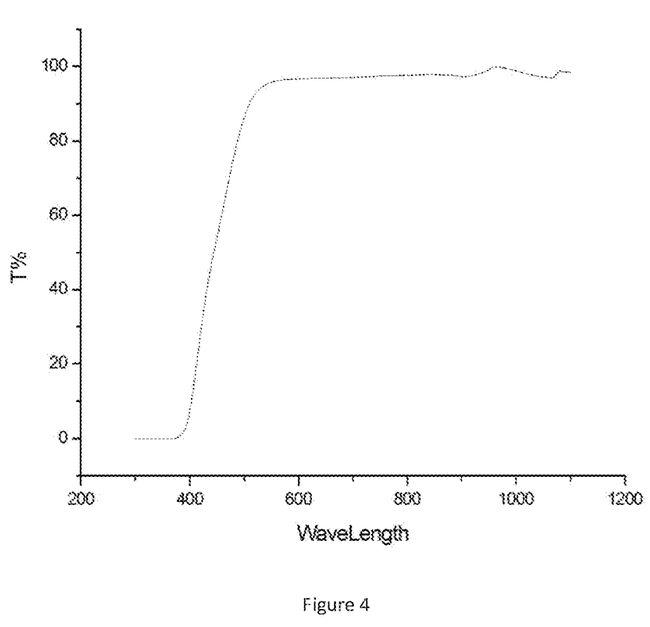
FIG. 4 illustrates the spectral transmittance curve of another specific embodiment 22.

This example illustrates a method for measuring the spectral transmittance of an intraocular lens to evaluate the spectral transmittance of the material. The transmittance of the intraocular lens made of the materials of Examples 6 and 22 in the visible region is measured by using a spectrophotometer, wherein the instrument is UV-3300 type UV-Vis spectrophotometer from MAPADA, which has a wavelength scanning range of 300-1100 nm. The spectral transmittance curve is shown in FIG. 3 and FIG. 4. Example 6 is an ultraviolet absorbing type, and Example 22 is a blue filtered type, which filter harmful ultraviolet and blue light. The average spectral transmittance in the visible light range is >95%, and the spectral transmission performance is excellent. It is suitable for preparing intraocular lens.

Example 29: Glass Transition Temperature Test of Prepared Material

Figure 5:
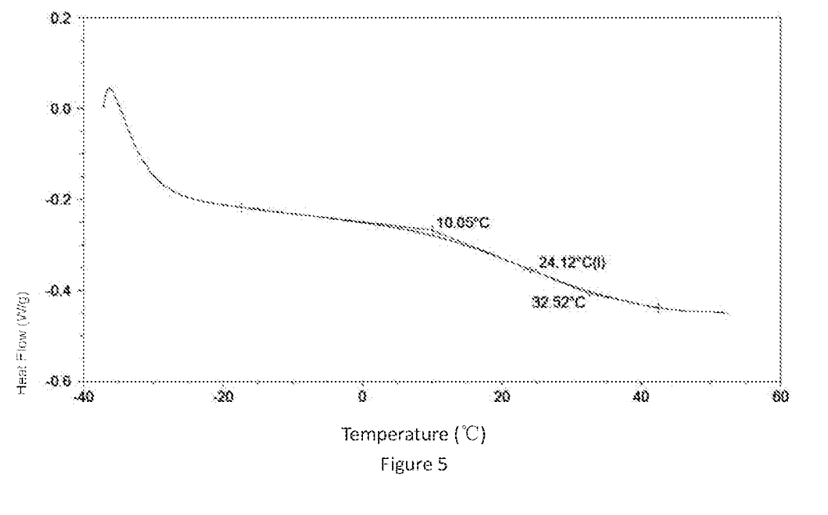
FIG. 5 illustrates the glass transition temperature of the material of Example 5.

This example illustrates the test method for the glass transition temperature of the material. The glass transition temperature of the material of Example 5 was tested by using Parallax Scanning calorimetry Analyzer Model Q20 from TA Instruments, USA, with 10 mg sample, at a temperature increase rate of 10° C. per minute, and a temperature scanning range of −35–60° C. After the software analysis, the glass transition temperature of the material was 24.12° C. The test results are shown in FIG. 5. The material softens slightly above room temperature and is suitable for punching into blanks. At the same time, it hardens slightly below room temperature, facilitates machining into intraocular lens, and it has a relatively moderate glass transition temperature, and is conducive to the large-scale production of intraocular lenses.

Example 30: Measurement of Refractive Index

This embodiment illustrates the method for measuring the refractive index of a material. The Abbe's refractometer was used to test the refractive state of the material of Example 21 in wet state and in dry state. The Abbe's refractometer is connected to the constant temperature water bath, and the temperature of the constant temperature water bath is set to 35° C. during the test. The refractive index of the dried material (i.e. the refractive index of the material in the dry state) is tested after balancing by using the test methods known to those skilled in the art. The value of the index of refraction of the material of Example 21 in dry state was 1.5158. The same piece of material was hydrated with physiological saline and placed in a constant temperature incubator at 35° C. for 7 days. The surface moisture was quickly wiped off and the refractive index was measured in the same manner as in the dry state. The refractive index of the material of Example 21 in wet state was 1.5038.

Example 31: Water Absorption Test of Materials

An object of the present invention is to develop a material having a medium water content suitable for use in the production of intraocular lens. This example illustrates the method for measuring the water content of a material. The prepared material was placed in physiological saline at 35° C. and fully hydrated to balance. After removing the material from the water, the moisture on its surface was quickly wiped off, measured the wet weight $m_1$. The material was then placed in a vacuum oven at 60° C., fully dried to a constant weight, and measured dry weight $m_2$. Calculate the water content of the material in its hydration equilibrium according to the formula "water content=$(m_1-m_2)/m_1$".

The water content of the material of Example 21 was measured according to the above method and the measured value was 5.1%.

Example 32: Test of a Glistening of an Example

This experimental example gives the test method for the glistening inside the material.

The glistening of the material is the main problem of affecting the ALCON AcrySof IOLS; the glistening means that there is a hole or a vacuole inside the material. A severe glistening affects the optical performance of the intraocular lens and brings severe post-operative problems. A test for the glistening inside the material was performed on the material of the present invention.

The material of Example 18 was processed into a disk shape, and the surface was turned and polished to be smooth. After cleaning, it was placed in an aqueous solution of BBS at 35° C. After being equilibrated for 10 days, it was observed under the irradiation of side light and observed under a 10× optical microscope. There was no glistening phenomenon. The surface was clear and translucent.

Example 33: Test of Adsorption Characteristics of Silicone Oil

This example illustrates the test method and test results of the adsorption property of the silicone oil of the material. First, the dye (oil red) was dissolved in an appropriate amount of ethanol and filtered to obtain an oil-red ethanol solution. This solution was added to the silicone oil and stirred for 6 hours to make it homogenously mixed. The dyed silicone oil was placed at 70° C. overnight to remove the ethanol. The sample to be tested was soaked in the BSS solution for 24 hours, removed, drained, placed in the dyed silica gel and soaked for 3 hours, drained with silicone oil, and re-placed in the BSS solution for 1 hour; photographed and analyzed the absorbability.

According to the above test method, the adsorption property of the silicone oil of the material of Example 18 was tested, and the result showed that the material of the present invention is not prone to adsorb the silicone oil.

Example 34: Calcium Deposition Test

This example illustrates test method and test results of the calcium deposition on the surface of the material. In 1994, Jensen et al. first reported that 11 cases of cataract patients had precipitated on the surface of the intraocular lens during and early after surgery. X-ray diffraction examination revealed that the precipitate contained hydroxyapatite calcium. Later studies showed that hydrophilic materials are more conducive to calcium deposition than hydrophobic materials, which is also a typical problem encountered in the clinical use of hydrophilic intraocular lens. The material sheet of the present invention and the comparative material were soaked in a suspension of hydroxyapatite, adsorbed for 24 hours, then immersed in BSS for 1 hour, and the material was placed in an alizarin red solution, and photographed to observe the staining condition. The area specifically stained with alizarin red is the hydroxyapatite adsorption area, which is a calcium deposition area.

The calcium deposition of the material of the present invention was tested according to the above test method. The test result shows that the material of the present invention is not prone to calcium deposition, and surface opacification is less prone to occur on the surface of the intraocular lens after implantation in the human body. Compared with the traditional hydrophilic intraocular lens material, the material of the invention can greatly reduce the probability of surface calcium deposition after implantation of the intraocular lens in a human body.

Example 35: Mechanical Properties of the Material (Elongation at Break and Fracture Strength after Complete Hydration)

The material of Example 6 was used as an example to illustrate the test of the mechanical properties of the material. The material obtained in Example 6 was hydrated in physiological saline at 35° C. for 7 days. After fully hydrated, the material was punched into a standard shape by using a punch conforming to Type IV in the ATSM D638 table.

The material was placed in a constant temperature water bath at 35° C. Using an electronic universal tensile testing machine, the mechanical properties of the material were tested in accordance with ATSM standards, and the tensile speed was selected to be 50 mm/min. Elongation at break and breaking strength were recorded and the test results are as follows.

| Ex. | larger/mm | thickness/mm | guage lengthL0/mm | elongation at break/% | tensile strength/Mpa |
|---|---|---|---|---|---|
| 6 | 5.98 | 1.85 | 25 | 225.67 | 2.97 |

Example 36: Simulated Implantation Test

All the intraocular lens processed in Example 27 were sequentially implanted during the simulated surgery, and a set of intraocular lens implantation system for cataract surgery was used, including an implanter and an import head. The end of the introduction head was different size according to the size of the surgical incision. The parameters of each model are shown in Table 3. The implanter should match the model of the introduction head. The specific operation process is as follows: firstly injected an appropriate amount of viscoelastic agent into the introduction head, used a tweezers to capture an intraocular lens, sent the intraocular lens into the introduction head and pushed it to the mark of the introduction head, and then installed the introduction head on the pusher, and waited for about 5 minutes to simulate the operation habit during surgery. Finally, the intraocular lens is implanted into a vessel filled with physiological saline, recorded whether the push-injection process is smooth, whether the intraocular lens smoothly unfold, and whether the introduction head is damaged or not. During the implantation experiment, the room temperature environment should be controlled at 25-30° C., the viscoelastic agent temperature should be controlled at 2-8° C., and the physiological saline should be controlled at 19-25° C.

TABLE 3

Parameters of different model of introduction headers

| model of introduction headers | Surgical incision/mm | introduction head outer diameter/mm | introduction head inner diameter/mm |
|---|---|---|---|
| SI-1 | 2.8 | 2.20 | 1.80 |
| SI-2 | 2.4 | 1.88 | 1.48 |
| SI-3 | 2.2 | 1.80 | 1.40 |
| SI-4 | 2.0 | 1.70 | 1.30 |
| SI-5 | 1.8 | 1.60 | 1.20 |

When all intraocular lenses were tested in simulated push-injection test by different sizes of introduction heads, the push-injection was very smooth, and there was no frustration during the push-injection. After the push-injection, no obvious cracking or bursting occurred at the end of all the introduction heads. After the entire implantation process was completed, all intraocular lenses completely unfolded within 3 to 10 seconds after being implanted into physiological saline through the introduction head, and were completely lossless.

The invention claimed is:
1. A material comprising a copolymer comprising hydrophilic acrylates monomers and hydrophobic acrylates monomers, wherein the molar ratio of the hydrophilic acrylates monomers to the hydrophobic acrylates monomers is from

42.5:57.5 to 45:55, wherein the hydrophilic acrylates monomers are selected from the group consisting of hydroxyethyl methacrylate, hydroxyethyl acrylate, hydroxypropyl methacrylate, hydroxypropyl acrylate, vinyl pyrrolidone, ethoxyethoxyethyl methacrylate, ethoxyethoxyethyl acrylate, ethoxyethyl methacrylate, ethoxyethyl acrylate, methoxyethyl methacrylate, methoxyethyl acrylate, 1,3-butylene glycol dimethacrylate, ethylene glycol dimethacrylate, polyethylene glycol methacrylate, polyethylene glycol 200 dimethacrylate, polyethylene glycol acrylate, poly(ethylene glycol) methyl ether methacrylate, polyethylene glycol methyl ether acrylate, glycidyl methacrylate, glycidyl acrylate, acrylic acid, methacrylic acid, 2-(trifluoromethyl) acrylic acid, phenyl acrylic acid, acrylamide, methacrylamide, N-methylol acrylamide, N-methylol methacrylamide, and a mixture thereof, wherein the hydrophobic acrylates monomers are selected from the group consisting of methyl methacrylate, ethyl methacrylate, ethyl acrylate, butyl methacrylate, butyl acrylate, hexyl methacrylate, hexyl acrylate, isopropyl methacrylate, isopropyl acrylate, isobutyl methacrylate, isobutyl acrylate, tert-butyl methacrylate, tert-butyl acrylate, isooctyl methacrylate, isooctyl acrylate, isodecyl acrylate, isodecyl methacrylate, lauryl methacrylate, lauryl acrylate, octadecyl methacrylate, octadecyl acrylate, 9-anthryl methyl methacrylate, 9-anthryl methyl acrylate, cyclohexyl methacrylate, cyclohexyl acrylate, dimethylaminoethyl acrylate, dimethylaminoethyl methacrylate, N,N-dimethylmethacrylamide, N,N-dimethylacrylamide, N,N-diethylaminoethyl acrylate, N,N-diethylaminoethyl methacrylate, N-tert-butyl acrylamide, N-tert-butyl methacrylamide, N-isopropyl acrylamide, N-isopropyl methacrylamide, tetrahydrofurfuryl methacrylate, tetrahydrofurfuryl acrylate, trifluoroethyl methacrylate, trifluoroethyl acrylate, hexafluorobutyl methacrylate, hexafluorobutyl acrylate, 2-perfluorodecylethyl acrylate, 2-perfluorodecylethyl methacrylate, 2-(perfluorooctyl)ethyl methacrylate, 2-(perfluorooctyl)ethyl acrylate, acetone glycidyl methacrylate, acetone glycidyl acrylate, tetrahydrofuryl acrylate, tetrahydrofurfuryl methacrylate, phenyl methacrylate, phenyl acrylate, phenylethyl methacrylate, phenylethyl acrylate, phenoxyethyl methacrylate, phenoxyethyl acrylate, benzyl methacrylate, benzyl acrylate, acetoacetoxyethyl methacrylate, acetoacetoxyethyl acrylate, diacetone acrylamide, diacetone methacrylamide, allyl methacrylate, phenoxyethyl acrylate, and a mixture thereof, and wherein the material has the following properties:

(a) a water content at 35° C. that is 5 to 8 wt %;
(b) a refractive index when the material is hydrated at 35° C. that is 1.49 to 1.54; and
(c) a glass transition temperature of 20 to 35° C., wherein the material is in a dry state, in which the refractive index of the material after water saturation satisfies this formula:

$$n = v_w n_w + (1-v_w) n_p$$

wherein $v_w$ is the water content, $n_w$ is the refractive index of water, and $n_p$ is the refractive index of the dry acrylate polymer.

2. The material according to claim 1 having a glass transition temperature of 20 to 30° C., wherein the material is in a dry state.

3. The material according to claim 1 having an elongation at break in a wet state that is more than 180% and a breaking strength when hydrated that is more than 2.5 MPa.

4. The material according to claim 1, further comprising at least one fluorescent agent and/or at least one photosensitizer;

wherein the at least one fluorescent agent and/or the at least one photosentitizer participate in the polymerization when forming the copolymer material; or the at least one fluorescent agent and/or the at least one photosentitizer are added to the copolymer material by physical dispersion when forming the copolymer material; or the at least one fluorescent agent and/or the at least one photosentitizer are fixed on the surface of the copolymer material by surface grafting or surface modification; or the at least one fluorescent agent and/or the at least one photosentitizer are fixed on the surface of the copolymer material by surface-coating.

5. The material according to claim 4 wherein the fluorescent agent is selected from the group consisting of fluorescein, cyanine fluorescent dyes, fluorescein isothiocyanate, fluorescent rhodamine substances, fluorescent lanthanide chelates, P-phycoerythrin (PE), substances that produce fluorescence upon enzyme action, Polypida chlorophyllin (PerCP), propidium iodide, a mixture of any of the above substances, and a nanomaterial having any of the above substances.

6. The material according to claim 4, wherein the photosensitizer is selected from the group consisting of indole monocyanine, indole carbocyanine, indole dicarbocyanine, indole tricarbocyanine, tricarbocyanine dyes, benzoindole semicyanine dyes, indole squarylium dyes, chlorophyll, pheophytin, pheophorbide a, dihydroporphine e6, purpurin 18, dihydroporphine p6, dihydroporphine f, protoporphyrin, hematoporphyrin (HpD), porfimer sodium, photocarcinorin (PSD-007), nanogold, nanotungsten oxides, nano-copper sulfides, nano-iron oxides, nano-nickel carbide, nano-molybdenum oxide, fluorescein O-acrylate and fluorescein O-methacrylate, other water-soluble or fat-soluble based on the modification of the above photosensitizers, and a mixture thereof.

7. A medical device or equipment made of the material according to claim 1, wherein the device or equipment is selected from the group consisting of an intraocular lens, a corneal contact lens, an orthokeratology lens, an iris hook, an artificial lens, an artificial cornea, a corneal inner ring, a capsular bag tension ring, an intracorneal lens, a glaucoma drainage valve, a drug sustained-release carrier, an intraocular filler, a fundus filler, glasses, goggles, a medical equipment lens, a medical treatment device and a medical detection device with fluorescent properties.

8. The material according to claim 1, wherein the water content at 35° C. is from 6 to 8 wt. %.

9. The material according to claim 1, wherein, the water content at 35° C. is from 7 to 8 wt. %.

10. The material according to claim 1, wherein, the refractive index at 35° C. is from 1.49 to 1.53.

11. The material according to claim 1, wherein, the refractive index at 35° C. is from 1.50 to 1.52.

12. The material according to claim 1, wherein the hydrophilic acrylates monomers are hydroxyethyl methacrylate.

13. The material according to claim 1, wherein the hydrophobic acrylates monomers are ethyl acrylate or phenoxyethyl acrylate.

14. The material according to claim 2, wherein the glass transition temperature is from 20 to 25° C.

* * * * *

UNITED STATES PATENT AND TRADEMARK OFFICE
CERTIFICATE OF CORRECTION

PATENT NO. : 11,318,226 B2
APPLICATION NO. : 15/776263
DATED : May 3, 2022
INVENTOR(S) : Sui et al.

It is certified that error appears in the above-identified patent and that said Letters Patent is hereby corrected as shown below:

In the Specification

Column 5, Line 27: Please correct "AGEFLEX"' to read --AGEFLEX™--

Column 8, Line 47: Please correct "is the volume" to read --$v_i$ is the volume--

Signed and Sealed this
Fifteenth Day of November, 2022

Katherine Kelly Vidal
*Director of the United States Patent and Trademark Office*